(12) United States Patent
Culver et al.

(10) Patent No.: US 7,974,881 B2
(45) Date of Patent: *Jul. 5, 2011

(54) METHOD AND SYSTEM FOR ASSESSING, SCORING, GROUPING AND PRESENTING NUTRITIONAL VALUE INFORMATION OF FOOD PRODUCTS

(75) Inventors: Stephen F. Culver, Cape Elizabeth, ME (US); Leslie M. Fischer, Durham, NC (US); James L. McBride, Windham, ME (US); Lisa A. Sutherland, Durham, NC (US); John A. Vitagliano, Charlotte, NC (US)

(73) Assignee: Guiding Stars Licensing Company, Scarborough, ME (US)

( * ) Notice: Subject to any disclaimer, the term of this patent is extended or adjusted under 35 U.S.C. 154(b) by 91 days.

This patent is subject to a terminal disclaimer.

(21) Appl. No.: 11/926,727

(22) Filed: Oct. 29, 2007

(65) Prior Publication Data

US 2008/0059342 A1 Mar. 6, 2008

Related U.S. Application Data

(63) Continuation of application No. 11/437,315, filed on May 19, 2006.

(51) Int. Cl.
*G06Q 30/00* (2006.01)
(52) U.S. Cl. .............................. 705/15; 426/72; 434/127
(58) Field of Classification Search .................... 426/72; 434/127; 705/15
See application file for complete search history.

(56) References Cited

U.S. PATENT DOCUMENTS

| 5,412,560 | A | * | 5/1995 | Dennison ..................... 600/300 |
| 5,478,989 | A | | 12/1995 | Shepley |
| 5,726,899 | A | | 3/1998 | Ferguson et al. |
| 5,819,735 | A | | 10/1998 | Mansfield et al. |
| 5,841,115 | A | * | 11/1998 | Shepley ....................... 235/375 |
| 6,246,998 | B1 | | 6/2001 | Matsumori |
| 6,358,546 | B1 | | 3/2002 | Bebiak et al. |
| 6,663,564 | B2 | | 12/2003 | Miller-Kovach et al. |
| 6,796,507 | B2 | | 9/2004 | Bean et al. |
| 7,044,739 | B2 | | 5/2006 | Matson |

(Continued)

FOREIGN PATENT DOCUMENTS

WO WO9803930 1/1998

OTHER PUBLICATIONS

Sugar and vending groups take offensive against obesity, Feb. 2005, Newsletter, Brief Article, Stagnito Communications.*

(Continued)

*Primary Examiner* — Matthew S Gart
*Assistant Examiner* — Talia Crawley
(74) *Attorney, Agent, or Firm* — Verrill Dana, LLP; Chris A. Caspiro (57) ABSTRACT

A method and system for presenting nutritional information about food products. The method involves gathering nutritional data about food products, analyzing that data to determine a nutritional value, scoring the product, and applying a designation reflecting the nutritional score. The nutritional value score designation is then displayed at the point of sale for observation by customers. The system includes a data gathering function, a data analyzing function, a data storing function, a scoring function, a reporting function and a display function to perform the steps of the method described.

28 Claims, 7 Drawing Sheets

U.S. PATENT DOCUMENTS

| | | | |
|---|---|---|---|
| 2002/0004749 | A1 | 1/2002 | Froseth et al. |
| 2003/0054089 | A1* | 3/2003 | Prosise et al. ............... 426/658 |
| 2003/0171944 | A1* | 9/2003 | Fine et al. ......................... 705/1 |
| 2003/0226695 | A1* | 12/2003 | Mault ........................ 177/25.16 |
| 2004/0078218 | A1 | 4/2004 | Badinelli |
| 2005/0042582 | A1* | 2/2005 | Graves ......................... 434/127 |
| 2005/0055860 | A1* | 3/2005 | Arrendale et al. ............. 40/637 |
| 2005/0086080 | A1 | 4/2005 | Stump et al. |
| 2005/0113649 | A1 | 5/2005 | Bergantino |
| 2005/0260302 | A1* | 11/2005 | Prosise .......................... 426/72 |
| 2006/0018998 | A1 | 1/2006 | Green et al. |
| 2006/0263750 | A1* | 11/2006 | Gordon ........................ 434/127 |
| 2006/0287810 | A1* | 12/2006 | Sadri et al. .................... 701/200 |
| 2007/0038933 | A1 | 2/2007 | Luzzatto |
| 2007/0059672 | A1 | 3/2007 | Shaw |
| 2008/0268103 | A1* | 10/2008 | Derks et al. ..................... 426/87 |

OTHER PUBLICATIONS

Vending Industry kicks off campaign targeting childhood obesity, Jan. 17, 2005, The Food Institute Report, No. 2, pp. 4.*

Aikman, S.N., et al., "Food attitudes, eating behavior and the information underlying food attitudes", Appetite, vol. 47, Issue 1, Jul. 2006, pp. 111-114, US.

Antonuk, Beth, et al., "The Effect of Single Serving Versus Entire Package Nutritional Information on Consumption Norms and Actual Consumption of a Snack Food", Journal of Nutritional Education and Behavior, vol. 38, Issue 6, Nov. 2006, pp. 365-370, US.

Blitstein, J.L., et al., "Use of Nutrition Facts Panels among Adults Who Make Household Food Purchasing Decisions", Journal of Nutrition Education and Behavior, vol. 38, Issue 6, Nov. 2006, pp. 360-364, US.

Bowman, S.A., "Food shoppers' nutrition attitudes and relationship to dietary and lifestyle practices", Nutrition Research, vol. 25, Issue 3, Mar. 2005, pp. 281-293, US.

Burton, S., et al., "Age, Product Nutrition, and Label Format Effects on Consumer Perceptions and Product Evaluations", Journal of Consumer Affairs, 30(1), pp. 68-69, US.

Chaftel, J.C., "Food and nutrition labeling in the European Union", Food Chemistry, vol. 93, Issue 3, Dec. 2005, pp. 531-550, US.

Charney, P.J. et al., "Reliability of Nutrition Diagnostic Labels When Used by Registered Dietitians at Three Levels of Practice", Journal of the American Dietetic Association, vol. 106, Issue 8, Supplement 1, Aug. 2006, p. A12, US.

Cunningham, J., et al., "Lessons learned from providing a free nutrition labeling tool for industry—the Australian experience", Journal of Food Composition and Analysis, vol. 17, No. 3-4, Jun.-Aug. 2004, pp. 565-574, US.

Edwards, J.U., et al., "Revision of the Food Guide Pyramid for Endurance Athletes Based on Carbohydrate Counting", Journal of the American Dietetic Association, vol. 99, Issue 9, Supplement 1, Sep. 1999, p. A38, US.

Grunert, K.G., et al., "A review of European research on consumer response to nutrition information on food labels", Journal of Public Health, US.

Hawthorne, K.M., et al., "An Educational Program Enhances Food Label Understanding of Young Adolescents", Journal of the American Dietetic Association, vol. 106, Issue 6, Jun. 2006, pp. 913-916, US.

Marietta, A.B., et al., "Older Americans and the Nutrition Facts Food Labels", Journal of the American Dietetic Association, vol. 97, Issue 9, Supplement 1, Sep. 1997, p. A113, US.

Moss, J., "Labeling of trans fatty acid content in food, regulations and limits—The FDA view", Atherosclerosis Supplements, vol. 7, Issue 2, May 2006, pp. 57-59, US.

Rothman, R.L., et al., "Patient Understanding of Food Labels: The Role of Literacy and Numeracy", American Journal of Preventive Medicine, vol. 31, Issue 5, Nov. 2006, pp. 391-398, US.

Satia, J.A., "Food nutrition label use is associated with demographic, behavioral, and psychosocial factors and dietary intake among African Americans in North Carolina", Journal of the American Dietetic Association, vol. 105, Issue 3, Mar. 2005, pp. 392-402, US.

Schoenbach, G., "An Attempt to Individualize Diabetes Medical Nutrition Therapy in Diabetes Classes", Journal of the American Dietetic Association, vol. 99, Issue 9, Supplement 1, September 199, p. A109, US.

Van Trijpa, Hans C.M., et al., "Consumer perceptions of nutrition health claims", Appetite, vol. 48, Issue 3, May 2007, pp. 305-324, US.

Screens "Wegmans Wellness Keys", (no date), website http://www.wegmans.com/eatwelllivewell/healthyEating/wellnessKey.asp (2 pages).

Screens "Have Food Allergies or Special Dietary Needs?", (May 6, 2005), http://www.wegmans.com/about/pressRoom/pressReleases/foodSensitivityEfforts.asp (2 pages).

Screen "Key in on Wellness Keys", (Feb. 1, 2006), http://www.wegmans.com/meb/columns/021106a.asp (1 page).

Screen "Key in on Wellness Keys", (Apr. 9, 2006), http://www.wegmans.com/meb/content.asp?contentid=64 (1 page).

Screen "Key in on Wellness Keys", (Apr. 15, 2006), http://www.wegmans.com/meb/columns/041506ML.asp (1 page).

Screens "How to Understand and Use Nutrition Facts Label", (Jun. 2000-Nov. 2004), http://www.cfsan.fda.gov/~dms/foodlab.html (10 pages).

Scott, J., "Nutrition Profiling—Guiding Consumer Choice." BEUC/TACD Conference (online), Dec. 1, 2005. [retrieved on Oct. 5, 2007]. Retrieved from the Internet: <URL: http://www.tacd.org/events/ge2/j_scott.ppt>. 19 pages.

Seddon, M., Soy and Soy-based Foods.? National Heart Foundation of New Zealand's Nutrition Advisory Committee [online], Mar. 1999. [retrieved on Oct. 5, 2007]. Retrieved from the Internet: <URL: http://nhf.org.nz/files/National%20Dietitian/Soy%20and%20Soy-based%20Foods_March1999.pfd>. 11 pages.

International Search Report and Written Opinion for PCT/US07/69130, date of mailing: Nov. 15, 2007, 7 pages.

Katz, D.L., "The Food Supply for Dummies," First Published Oct. 6, 2003 in the Hartford Courant, Carolyn Lumsden, Op-Ed Editor, 4 pages.

Rayner, M., et al., "Nutrient profiles: Development of Final Mode, Final Report." British Heart Foundation Health Promotion Research Group, Department of Public Health, University of Oxford, Dec. 2005, 86 pages.

Western Australia Department of Health Submission to the Australian Communications and Media Authority Review of its Children's Television Standards, Nov. 2005, 13 pages.

Underwood, A., "Three-Star Snacks in Aisle Five", Newsweek, Nov. 12, 2007, 1 page.

Drewnowski, A., "Concept of a nutritious food: toward a nutrient density score", The American Journal of Clinical Nutrition, 2005, 721-732, vol. 82, American Society for Clinical Nutrition, US.

Zelman, K. et al., "Naturally Nutrient Rich . . . Putting More Power on Americans' Plates", Nutrition Today, Mar./Apr. 2005, 60-68, vol. 40, No. 2.

Scarborough, P. et al., "Developing nutrient profile models: a systematic approach", Public Health Nutrition, 2007, 330-336, vol. 10(4), The Authors, UK.

Rayner, M. et al., "Nutrient profiles: Applicability of currently proposed model for uses in relation to promotion of food to children aged 5-10 and adults", British Heart Foundation Health Promotion Research Group, Department of Public Health, University of Oxford, Jan. 2005, 14 pages, UK.

Darmon, N. et al., "A Nutrient Density Standard for Vegetables and Fruits: Nutrients per Calorie and Nutrients per Unit Cost", Journal of the American Dietetic Association, 2005, 1881-1887, American Dietetic Association, US.

Rayner, M. et al., "Nutrient profiles: Further refinement and testing of Model SSCg3d", British Heart Foundation Health Promotion Research Group, Department of Public Health, University of Oxford, Sep. 2005, 60 pages, UK.

* cited by examiner

| Negative Attributes/Weighting→ ↓ | 0 | -1 | -2 | -3 | -10 |
|---|---|---|---|---|---|
| *Trans* fat | None (0 on Facts Panel and not listed in ingredients) | <0.5 g | 0.5-1.0 g | >1.0 g | -- |
| Saturated fat | ≤1 g (5% DV) | >1-2 g (10% DV) | >2-3 g (15% DV) | >3 g | -- |
| Cholesterol | ≤15 mg (5%DV) | ≤30 mg (10%DV) | ≤45 mg (15%DV) | >45 mg | -- |
| Added sugars | NA | ≤10% kcal | ≤25% kcal | ≤50% kcal | >50% kcal |
| Added Sodium | ≤120 mg (5%DV) | ≤240 mg (10%DV) | ≤360 mg (15%DV) | ≤600 mg (25%DV) | >600 mg |
| | | | | | |
| Positive Attributes/Weighting→ ↓ | 3 | 2 | 1 | 0 | -- |
| Dietary fiber | ≥3.75 g (15%DV) | ≥2.5 g (10%DV) | ≥1.25 g (5%DV) | <1.25 g | -- |
| Nutrient Density | ≥10%DV of 2 or more nutrients | ≥10%DV of 1 or more nutrients OR ≥5%DV of 2 or more nutrients | ≥5%DV of 1 nutrient | -- | -- |

| Elements/Bonus Value→ ↓ | +1 | -1 |
|---|---|---|
| Whole grain | X | |

FIG. 5

| Negative Attributes/Weighting→ ↓ | 0 | -1 | -2 | -3 | -10 |
|---|---|---|---|---|---|
| *Trans* fat | None (0 g on Facts Panel and not listed in ingredients) | <0.5 g | .05-1.0 g | >1.0 g | -- |
| Saturated fat | ≤1.5 g (7.5% DV) | >1.5-2 g (10% DV) | >2-3 g (15% DV) | >3 g | -- |
| Cholesterol | ≤60 mg (20% DV) | ≤90 mg (30% DV) | ≤120 mg (40% DV) | >120 mg | -- |
| Added sugars | NA | ≤10% kcal | ≤25% kcal | >25% kcal | -- |
| Added Sodium | ≤120 mg (5%DV) | ≤240 mg (10%DV) | ≤360 mg (15%DV) | ≤600 mg (25%DV) | >600 mg |
| Positive Attributes/Weighting→ ↓ | 3 | 2 | 1 | 0 | -- |
| Nutrient Density | ≥10%DV of 2 or more nutrients | ≥10%DV of 1 or more nutrients OR ≥5%DV of 2 or more nutrients | ≥5%DV of 1 nutrient | NR | -- |

FIG. 6

| Scoring/Group→ ↓ | -- | ☆ | ☆ ☆ | ☆☆☆ |
|---|---|---|---|---|
| Total points for general foods and beverages | <1 | 1-2 | 3-4 | 5-7 |
| Total points for meats, poultry, seafood, dairy and nuts | <1 | 1 | 2 | 3 |

FIG. 7

METHOD AND SYSTEM FOR ASSESSING, SCORING, GROUPING AND PRESENTING NUTRITIONAL VALUE INFORMATION OF FOOD PRODUCTS

CROSS REFERENCE TO RELATED APPLICATION

The present application is a continuation of, and claims priority benefit in, U.S. nonprovisional application Ser. No. 11/437,315, filed May 19, 2006, entitled "METHOD AND SYSTEM FOR ASSESSING, SCORING, GROUPING AND PRESENTING NUTRITIONAL VALUE INFORMATION OF FOOD PRODUCTS" assigned to a common assignee. The entire content of that priority application is incorporated herein by reference.

BACKGROUND OF THE INVENTION

1. Field of the Invention

The present invention relates to retail food sales. In particular, the present invention relates to characterizing the nutritional value of foods in a standardized way, establishing food nutritional value designations, and presenting that information in a readily observable manner.

2. Description of the Prior Art

Current literature documents the growing problems of obesity, heart disease, cancer, and other diseases that may be prevented or mitigated by healthy eating and lifestyle choices. The public is inundated with information about the dangers of certain types of foods and the benefits of others. It is difficult for consumers to keep current with the latest research and to synthesize that information into meaningful purchasing decisions at the grocery store.

The retail food sales business is extremely competitive. Because competition on price alone is not always possible or effective, food retailers often look for other ways to distinguish themselves from their competitors. Customer service is one of the more effective ways for food retailers to compete. One such customer service is providing information about the food products. As consumers become more health-conscious, they are more inclined to shop at food retailers that regularly provide helpful, accurate and consistent information about the effects that the food products being offered might have on consumer health.

Much of the information presented to the consumer at the point of sale is inadequate for a number of reasons. The information provided is not based upon one set of uniform standards. Product packaging and marketing materials may or may not contain information about healthy attributes of the products depending upon the marketing strategy of the manufacturer. Even when such information does appear, it may be incomplete, confusing or inaccurate. Some such information consists of the endorsement of the product by a health-related entity, for which the manufacturer has paid a fee. Another type of such information consists of a health designation based upon consideration of a very limited set of criteria in order to produce a desired result. Some information is simply nutritional data for selected nutrients, while other less desirable ingredients are ignored.

It is also noteworthy that much of the information comes not from the retailer, but from the manufacturer. Manufacturer's designations are, by definition, limited to their own products and do not provide information about competing products. This limitation precludes a meaningful comparison of competing products of different brands. Given the manufacturer's vested interest in selling as many of its products as possible, consumers may question the accuracy or completeness of the manufacturer's designations as well.

Nor is it always practical for consumers to rely upon the nutritional information and ingredient lists or lists of nutritional data on product labels. To do so would require the consumer to spend a significant amount of time reading and analyzing the information on the product label. The nutritional data are subject to manipulation by varying the serving size. Because there is no standardized serving size, manufacturers may, for example, artificially reduce the serving size to reduce the quantity of kilocalories or fat disclosed on the label, thereby making the product appear more healthy than it actually is. Relying upon such lists can therefore be too time consuming and unreliable.

Specific examples of existing methods of providing health related information about food products illustrate many of these shortcomings. Most methods involve the use of designations, often consisting of a label alerting the consumer to a particular characteristic of the product. For instance, the method employed by Wegmans Food Markets, Inc., a food retailer based in Rochester, N.Y., ("Wegmans") uses 13 labels identifying characteristics such as "gluten free", "vegan", "high fiber", and "heart healthy". Wegmans only designates the products sold under its own brands, and does not designate the products sold under other brands. Another such system is the "smart shopping" certification offered by the American Heart Association to certain manufacturers who choose to participate in the program. This system "certifies" food products as "heart-healthy". Certified food products may then display a designation recognizable to consumers. Like the Wegmans method, this system is not employed universally across different brands because only the participating manufacturer's branded products are graded. The vast majority of food products displayed in a grocery store are therefore left ungraded. It is often impossible to use such systems to compare the participating manufacturer's products to competing products. These systems also rely upon a very limited set of criteria. The heart healthy designation is given to any food that contains fat, sodium, and cholesterol below a certain level and at least one nutrient (vitamin A, C, calcium, iron, protein or fiber) in an amount above a certain level. Many of the other ingredients that affect health are not considered. That is, there is not a comprehensive identification of overall potential effects of the product on human health based on the complete nutritional profile.

Another type of designation system involves providing basic nutritional data without comprehensive analysis, such as the nutritional information label required by the United States Food and Drug Administration ("FDA"), or labels that tout a certain level of a certain ingredient or nutrient. Basic nutritional data is information relating to the amounts of substances affecting human health contained in the food product. The FDA label provides the quantities of a government-established list of certain nutrients contained in a serving size. The problem with these methods is that they provide basic data only, and the consumer must analyze that data to determine the potential health effects of the product based on nutritional value. Certain substances that may affect the health characteristics of a product may be omitted from the nutritional data, but may appear on the ingredients list. It might not be apparent or convenient for customers to consult both lists. Another problem is that there is no standard serving size, so the serving sizes on competing products could differ, which would cause a misleading comparison between the two products unless the consumer is savvy enough to adjust the data from one of the products to account for the difference in serving size.

There are several limitations associated with such conventional methods. First, they merely provide a single particular characteristic designation rather than an overall scoring system. Second, they do not score all food products. Third, they do not provide comprehensive information at the point of sale. Fourth, they rely upon limited criteria, and thus are subject to the limitations of those criteria. Fifth, they are limited to assessing a product characteristic that may affect one aspect of healthiness rather than considering the food product as a whole for a more complete sense of the possible nutritional value of the product. Sixth, no standardization of serving size exists within food product groups. What is needed is a system that addresses the barriers that often prevent customers from making healthy choices—inconsistency, inaccuracy, inconvenience and confusion. There is therefore a great demand for a simple, comprehensive, accurate, and easy to understand system of communicating to consumers the relative nutritional values of food products at the point of sale. It would be advantageous for a food retailer to employ such a system as it would distinguish the food retailer from its competitors and enable the food retailer to develop substantial good will and loyalty with its customers.

SUMMARY OF THE INVENTION

An objective of this invention is to provide a simple, uniform, comprehensive, accurate, and reliable method of providing nutritional value information to the consumer for food products at the point of sale. Another objective of this invention is to provide a method for food retailers to distinguish themselves from their competitors and to create customer loyalty by offering such reliable nutritional value information in which customers can have confidence and upon which customers can rely. Another objective of this invention is to provide a method for analyzing a product's nutritional value as an aid to consumers in considering possible health characteristics of the product that is also practical for use by food retailers. Another objective of this invention is to provide a method of scoring food for nutritional value in a way that is useful to consumers.

These and other objectives are achieved by the present invention, which is a food nutritional value navigation system to make it easy for customers to find and buy products in retail food stores having nutritional characteristics of interest to them. The system generally includes an advisory panel, an algorithm for uniform scoring of food products, a collection of nutritional data about each food product suitable for use by the algorithm, an appropriate assessment and weighting of the various categories of information, a series of designations that communicate relative nutritional values of the food products to consumers, a store-wide system that scores products from all suppliers, and scoring for prepared as well as prepackaged foods. Prepared foods are those made at the retailer's premises such as freshly baked breads or freshly made sandwiches.

The advisory panel preferably has members with varied backgrounds suitable for providing guidance for improving the system and keeping it current with trends in nutrition and health sciences. Serving sizes are standardized to enable effective comparisons across brands. One way to standardize serving sizes is to make them realistic in the sense that they reflect the amount of the product that an average consumer is likely to consume at a single meal. Alternatively, they may be normalized to a predetermined weight or caloric value. For instance, for the sake of analysis, all serving sizes can be normalized to 100 kilocalories. (It is to be understood that the word "kilocalories" will be used throughout this description in any standardizing or normalizing discussions, as being the same as what is generally considered by the consuming public as "calories.") The scoring algorithm takes the basic data from the collection of data, usually a database, and computes a score. The weighting of the various elements of the data used in the performance of the scoring algorithm is reviewed and updated regularly. A simple and clear system of designations, such as three stars for the best nutritional value, two stars for better nutritional value, one star for good nutritional value, and no star for foods with limited nutritional value, is employed to communicate the scoring to consumers. This system is also unique in that it covers all food products in the store from all manufacturers and includes prepared as well as packaged products. These and the other advantages of the food nutrition scoring system of the present invention will become more apparent upon review of the following detailed description, accompanying drawings and appended claims.

DETAILED DESCRIPTION OF THE PREFERRED EMBODIMENT

Figure 1:
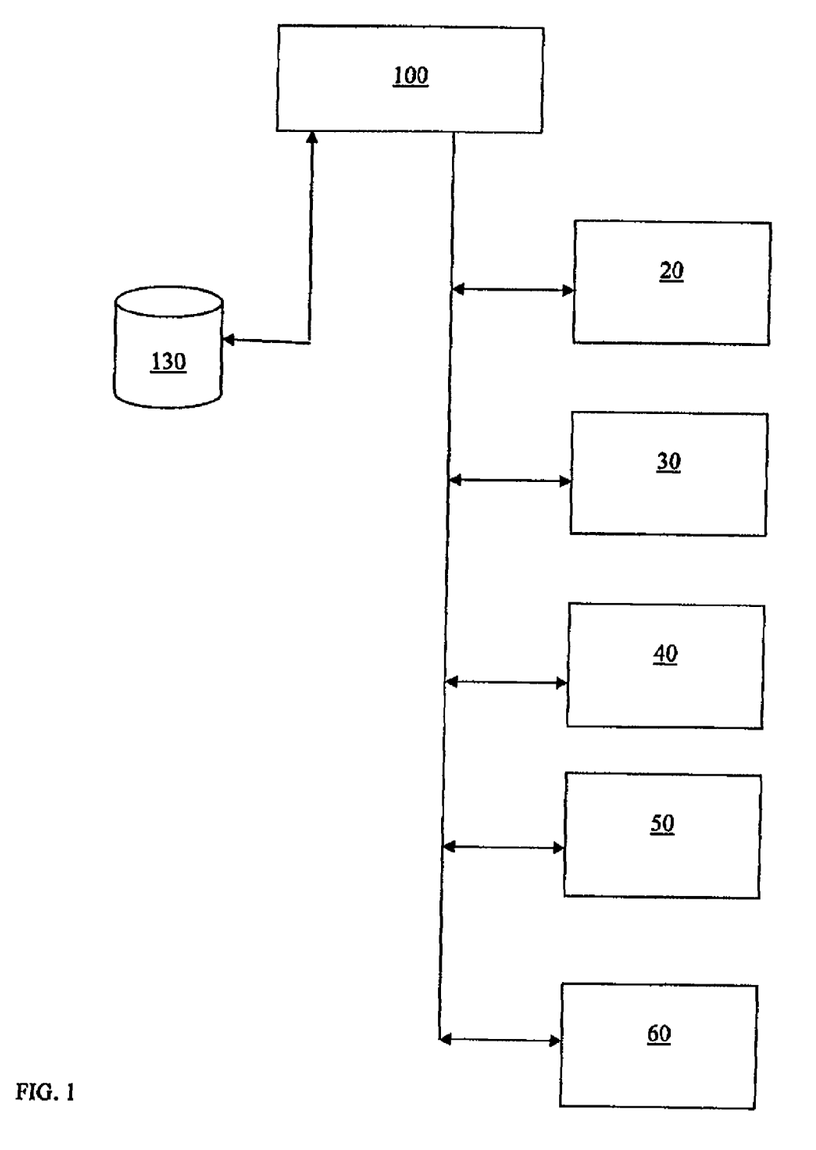
FIG. 1 is a block diagram of the functional elements of the system of the present invention.
Figure 2:
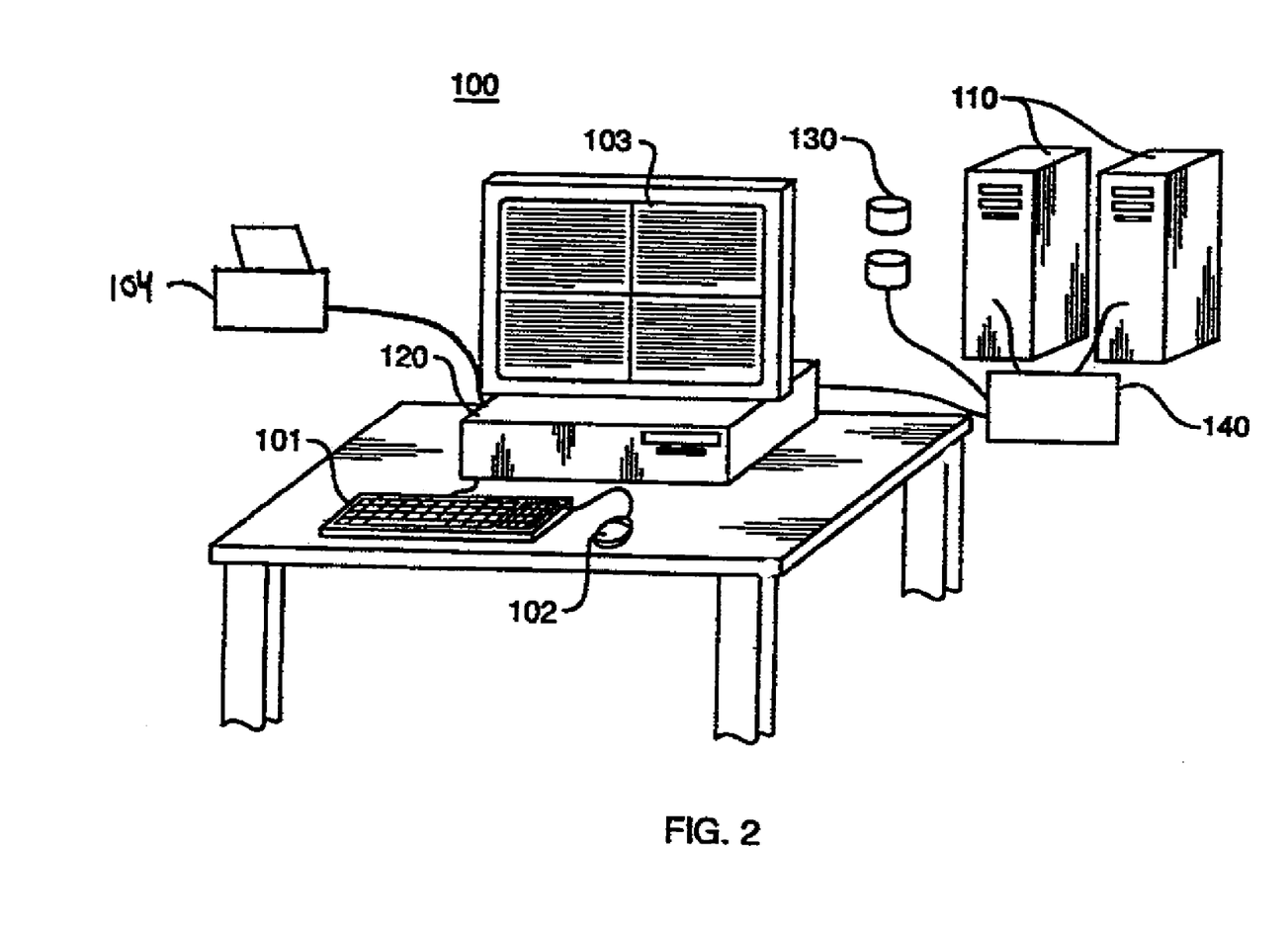
FIG. 2 is a simplified diagrammatic representation of an example computing system including the scoring system of the present invention.
Figure 3:
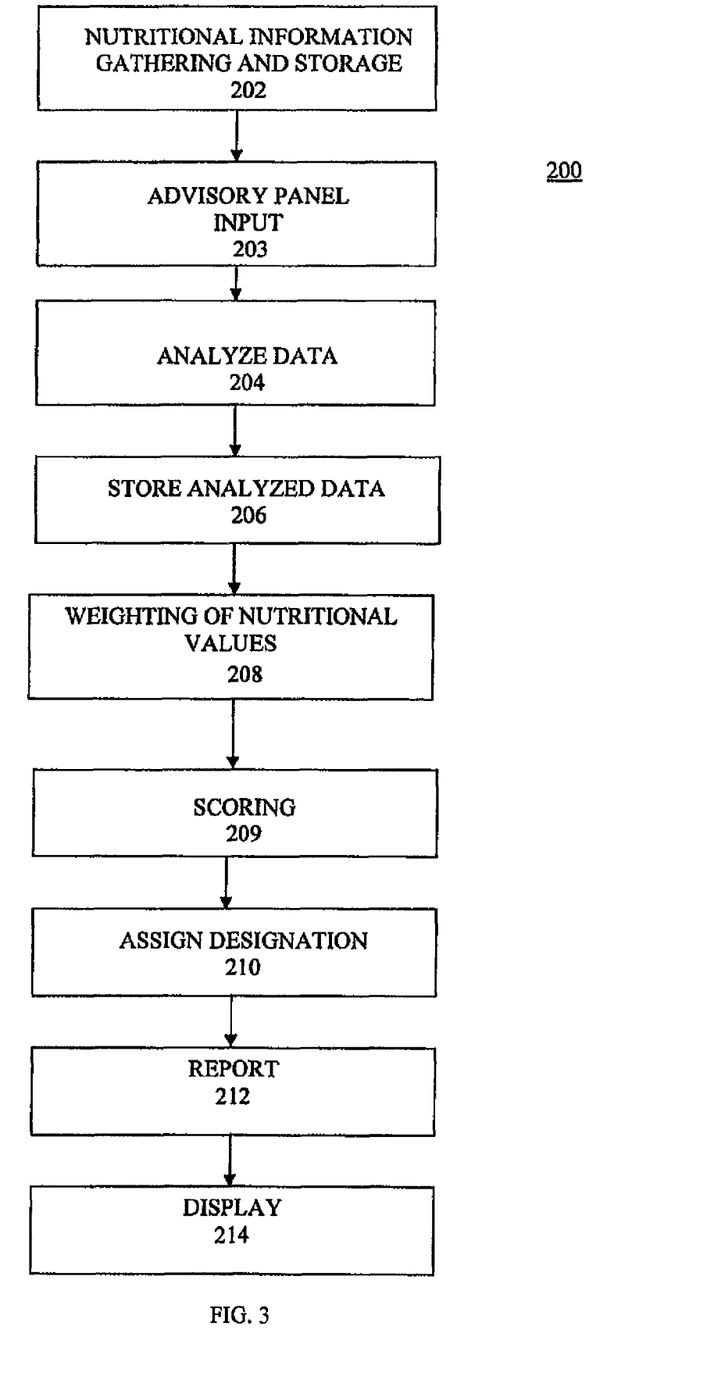
FIG. 3 is a simplified flow diagram representing the primary steps of the method of the present invention.
Figure 4:
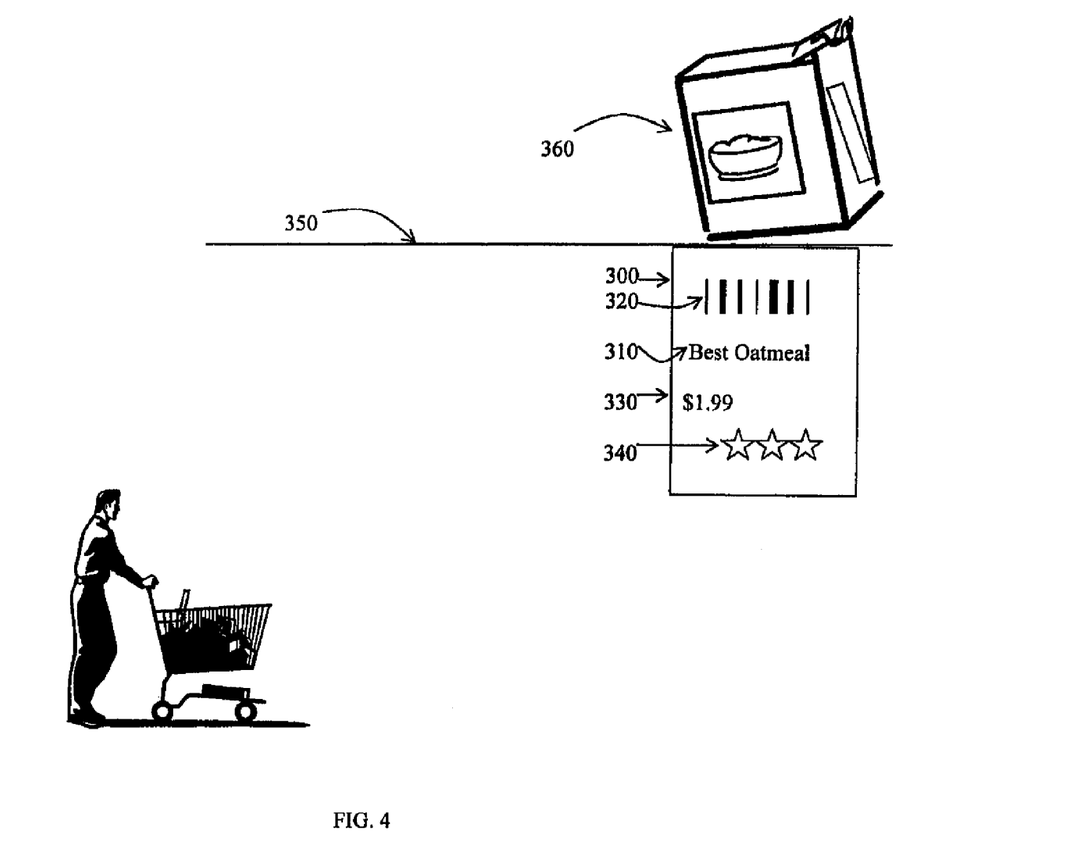
FIG. 4 is a representation of a display featuring the three star scoring designation.

The present invention is a food nutrition scoring system 10 represented functionally and diagrammatically in FIGS. 1 and 2, and a related method 200, represented in FIG. 3, for offering food products by retailers in a manner that provides meaningful, consistent, and accurate information to consumers at the point of sale. An example of the resulting output from the system 10 is shown in FIG. 4.

The system 10 shown in FIG. 1 includes a data gathering function 20, a data filtering function 30, data storing functions 40, a scoring function 50, and a reporting function 60. A computer system 100 as shown in exemplar form in FIG. 2 is preferably used as the means by which the functions described are performed. One or more accessible databases 130 are used to store and query information.

The data gathering function 20 may involve creating new data or accessing existing data. Nutrition data may not exist for some food products, especially prepared foods. Creating new data may involve measuring and analyzing ingredients of food products. Ingredient information may be used to determine nutritional information. Data gathering may include one or more manual methods such as recording information from product labels, or one or more automated methods such as electronic data transfer or scanning to input food nutrition information. It may be preferable to obtain nutrition information from the product label for pre-packaged food items. It may be possible to access existing data by licensing or purchasing rights to access such existing data.

The data filtering function 30 involves analyzing the data to determine its relative importance with respect to the nutritional value of the product. This function may occur in conjunction with the data gathering function 20 or after the data gathering function is completed. It may be necessary to manipulate the data to account for the proper serving size. Most product labels display nutritional data per serving size. There is no uniform standard for determining serving size. Two serving sizes are generally identified: volume and/or unit quantity (e.g. one cup of cereal or three cookies). The lack of uniformity hinders comparison because serving size (and thus nutritional data) may be inconsistent between products. Serving size therefore must be normalized for the purpose of comparing products. Any adjustments to the serving size would require a proportional adjustment to the other nutritional data. For example, if one manufacturer provides nutritional information for one cup of cereal and another for one and one-half cups, the latter could be normalized to one cup, with nutritional values reduced by 33⅓ percent. The preferred method of the present invention for normalizing the nutritional data for comparison is to adjust for a predetermined number of kilocalories. For instance, the nutritional data can be normalized to 100 kilocalories regardless of stated serving size. The data filtering function 30 performs this optional function by normalizing to a serving size of 100 kilocalories. Other normalizing functions may be used.

The use of standardization or normalization to 100 kilocalories resolves several limitations associated with standardization to the weight of a serving size. A preliminary comparative analysis using manufacturer-provided serving sizes, a universal serving size of 100 grams, and a kcal normalized serving size that supplies 100 kilocalories, indicates that the kcal normalized serving size may be optimal. The majority of dietary recommendations made by the key health organizations are based on percentages of the daily values of key macro- and micronutrients. The percentages of the daily values in turn are based on fixed caloric intakes. Thus in order to make the system of the present invention most consistent with these recommendations, it follows that the cutoffs used should likewise be linked to kilocalories rather than weight. Moreover, when a fixed weight serving size is used, many unrealistic serving sizes are evaluated. However, normalization to a 100 kilocalorie serving size adjusts serving sizes up or down inversely to caloric density. As higher caloric density foods (i.e. oils) tend to be consumed in smaller portions and vice versa, a 100 kilocalorie portion represents a more realistic serving size for more foods. In addition, normalization to a 100 kilocalorie portion can also be applied to beverages and liquid products which are supplied in volume rather than weight units. Using a commercially available yogurt product as an example, if the manufacturer's serving size is shown to be 64 g (2.25 oz.), and contains 80 kilocalories, to evaluate a normalized serving size that contains 100 kilocalories, all information on the nutrition facts panel would be multiplied by 1.25 (100 kcal/80 kcal).

The data storing function 40 preferably involves transferring data to one or more databases. Data can be stored after it is gathered and before it is filtered, or it can be filtered first then stored. It is preferable that both are done. Filtered data should preferably include at least the Uniform Product Code ("UPC"), and the nutritional data per 100 kilocalories of product as determined by the data filtering function 30. The data are then extracted from the database and analyzed by the scoring function 50. The data storing function 40 may also store scoring information to one or more of the databases 130 after the scoring function 50 is performed.

The scoring function 50 preferably includes an algorithm that automatically computes a score of nutritional quality. The algorithm may consider the amounts of the following substances in the food product: trans fat, saturated fat, cholesterol, added sugar, added sodium, dietary fiber, nutrient density and whole grain. These substances are believed to be important to the overall nutritional value of food products. Other substances or combinations of substances may be used as the understanding of the nutritional importance of such substances increases. For example, the impact of omega-3 fatty acids, plant phytosterols, monounsaturated fatty acid, live active cultures, nitrates, nitrites, phytochemicals, and phosphates may be considered.

The results of the scoring are reviewed and revised as necessary by the advisory panel to ensure the integrity of the system. The preferred scoring system is composed of three designations: three stars for the best nutritional value, two stars for better nutritional value and one star for good nutritional value. Foods with scores placing them below the one-star range would have no star designation. More or less complex groupings and designations may be included.

The reporting function 60 presents the scoring results in a desirable manner. One such manner is a printed label bearing the scoring designation that can be displayed along with the product at the point of sale as illustrated in FIG. 4. FIG. 4 shows a tag 300 that can be displayed at the point of sale. The tag 300 shows the product name 310, the Uniform Product Code ("UPC") 320, the price 330 and the scoring designation 340. The tag 300 may be removably applied to a shelf 350 upon which the products 360 are presented for sale. Other manners of displaying the scoring designations include a sign, a printed or electronic report, package labels, hand-held electronic device, and lists posted on the Internet or in the store.

As illustrated in FIG. 2, a user of the system 10 may engage in the evaluation of a food product through the computer system 100 that may be associated with local or remote computing means, such as one or more central computers, such as server 110 in a local area network, a metropolitan area network, a wide area network, or through intranet and internet connections. The computer system 100 may include one or more discrete computer processor devices, such as a desktop computer 120. The server 110, the computer processor 120, or a combination of both may be programmed to include one or more of the functions of the system 10. One or more databases represented by database 130 that may be associated with the server 110, the computer processor 120, other computing devices, or any combination thereof, include information related to the use of the system 10. The database 130 may be populated and updated with information necessary for carrying out one or more of the functions associated with the system 10. All of the devices may be interconnected through one or more signal exchange devices, such as router/switch 140.

In operation, a user of the system 10 inputs nutritional information through one or more input devices, such as a keyboard 101, a mouse 102, or a combination thereof, as well as any other input means suitable for directing information and requests to the server 110 and/or the processor 120. The input information, queries, and output information may be viewed on a computer display 103. Optionally, a local or remote printer 104 may be employed to print out input information, query information, and/or output information. It is to be noted that the system may be accessed and used through other forms of hardware devices including, for example, text/graphic scanner or reader inputs, touch-screen technology, voice recognition/synthesis equipment, other input/output devices, portable laptop, notebook, in-vehicle, or handheld personal digital assistant (PDA) portable computer devices, including those equipped for wireless communications, and telephony devices, such as wireless phones and IP-based phones. Other data collection and analysis systems may be employed.

As illustrated in FIG. 3, the method 200 of the present invention embodied in the system 10, or other system with equivalent functionality, aids retailers in providing food nutritional value scoring information to consumers. A first gathering and storing nutritional information step 202 can be performed in many ways. For example, data from the product labels can be entered into a computer device such as server 110 or processor 120 using the keyboard 101 and mouse 102 or some similar device. Data might also be available in electronic form from the product manufacturer or other sources. Advisory panel input step 203, which may be associated with either or both of the data filtering function 30 and/or the scoring function 50, involves receiving input from a panel of knowledgeable individuals regarding important nutritional elements of a food product and how each such element should be valued. Preferably, the advisory panel assists in the identification of nutritional element characteristics of food products and in the development of the system 10 for analyzing the data in a desirable way.

With continuing reference to FIG. 3, a data analysis step 204 associated with the data filtering function 30 to identify the nutritional elements determined to be of value by the advisory panel and, optionally, to standardize the gathered data to standard serving sizes or to a standard caloric value. A store analyzed data step 206 of the data storing function 40 includes transferring the analyzed nutritional element information of importance to the server 110, processor 120, and/or the database 130 for subsequent manipulation in determining the nutritional scoring of the food products selected for evaluation. The scoring of the food products includes a weighting of nutritional values step 208 of the scoring function 50 to assign relative importance to each of the nutritional elements identified and stored in the store analyzed data step 206. The weighting step 208 may assign a range of calculation weighting values as desired and as preferably recommended by the advisory panel. For example, a scale from 1 to 10 for a set of ten ranges of nutritional element values, a scale of −3 to +3 for a set of seven ranges of nutritional element values, or other type of scale may be assigned to weight the particular nutritional elements determined to be of importance. An example weighting matrix is presented in FIG. 5 and will be described herein with respect to several scoring examples. Once weighting values have been established, the nutritional element values may be manipulated by a calculation algorithm to establish a single score for the food product pursuant to a scoring step 209.

Figure 5:
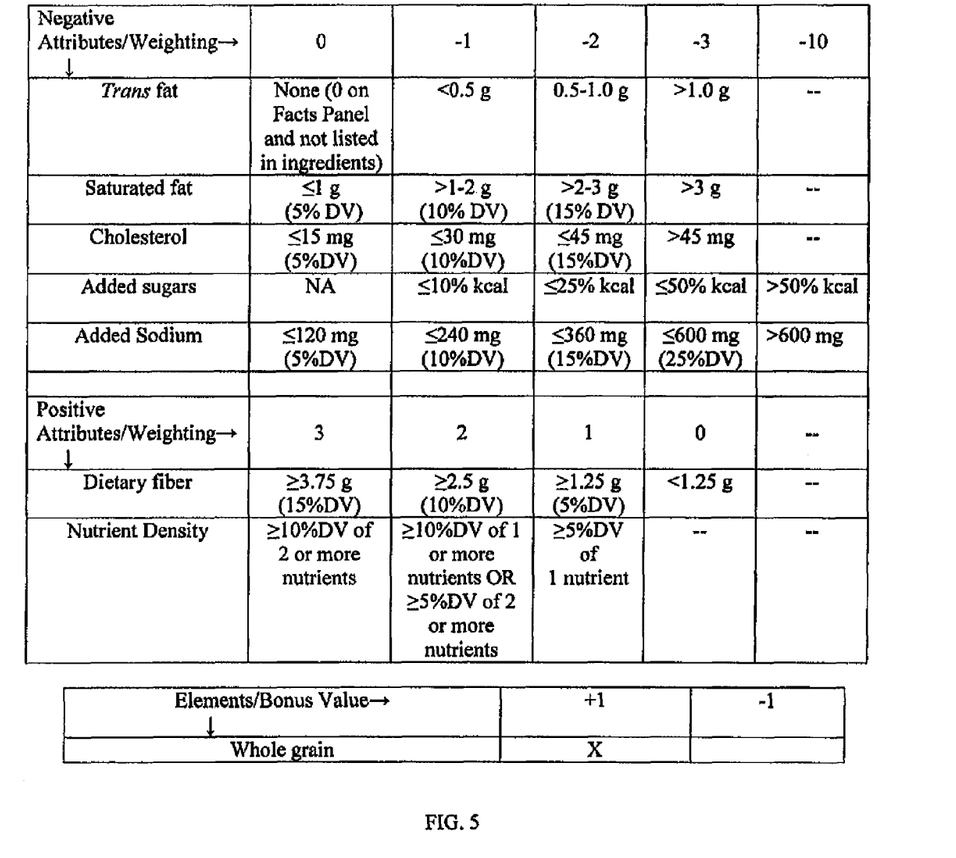
FIG. 5 is a table illustrating an example matrix of designated nutritional characteristics and weightings for the specific values of those characteristics used in the algorithm to establish food scoring information for general foods and beverages.
Figure 6:
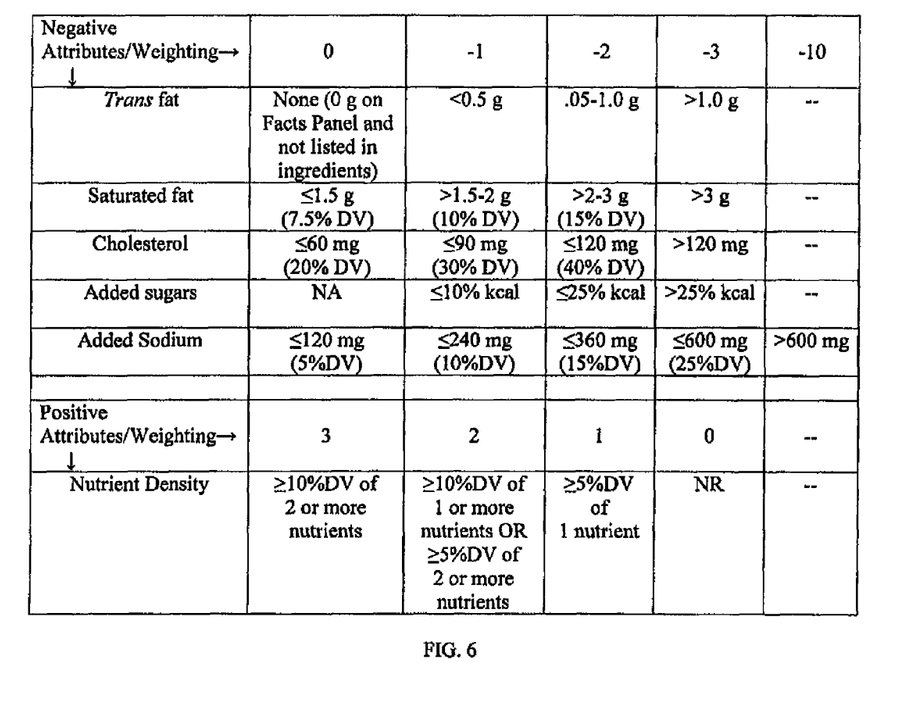
FIG. 6 is a table illustrating an example matrix of designated nutritional characteristics and weightings for the specific values of those characteristics used in the algorithm to establish food scoring information for meats, poultry, seafood, dairy and nuts.

As noted, the step of weighting the values 208 involves assigning greater or less relative value to the particular datum, in the form of a nutritional element characteristic, under consideration as a portion of the particular food product. Weighting matrices such as the examples shown in FIGS. 5 and 6 are useful for that purpose. FIG. 5 shows a first example matrix for general foods and beverages and FIG. 6 shows a second matrix for meats, poultry, seafood, dairy and nuts. In the example matrixes, seven primary nutritional elements of interest for any food product are shown in the first column, and weightings are assigned to the values of those nutritional elements dependent upon the particular value or range of the value. Each element value range is weighted by assigning a numerical point value to it. For instance, a general food and beverage product having less than 120 mg of sodium and 3 grams of dietary fiber would be given a "0" and a "2" point, respectively. This continues for all of the nutritional elements established by the advisory panel. Detailed descriptions of the particular nutritional elements used in the weighting matrices of FIGS. 5 and 6 are provided herein. Additional optional nutritional elements that may be considered but not specified in the examples presented herein are also described in detail herein. The relative overall nutritional value of a particular food product may then be established using these matrixes, or ones like them, and carrying out the scoring step 209.

The following detailed descriptions of the nutritional elements preferably considered in assigning nutritional food groupings are generally available from the product's Nutrition Facts panel and are the subject of the matrixes of FIGS. 5 and 6. Weightings of each are also described.

1. Trans fat—As of Jan. 1, 2006, this element must be listed as trans Fat on the Nutrition Facts panel of a product. If trans Fat is not listed on the Nutrition Facts panel, but the words "partially hydrogenated" (vegetable oil) appear in ingredient list, then food should be awarded −2 points for this element. Trans Fats are included in the model of the present invention because the Institute of Medicine has concluded that there is no safe level of trans fats in the diet. Moreover, numerous studies have shown that trans Fats have adverse effects on blood lipids—raising LDL ("bad") cholesterol, and lowering HDL ("good") cholesterol, thereby increasing the risk of heart disease. FDA labeling regulations allow any amount <0.5 g to be listed as 0 grams on the Nutrition Facts panel. However, a product must truly contain no trans Fat (0 grams listed on the Nutrition Facts panel and the words "partially hydrogenated" do not appear in ingredients) to get the best score (0 points). Foods that list having 0 grams of trans Fat on the Nutrition Facts panel but still contain partially hydrogenated vegetable oils are awarded −1 point 2. Saturated fat—listed as Saturated Fat on Nutrition Facts panel. In the general foods and beverages matrix of FIG. 5, the food product must contain ≦1 g of this element in order to receive the highest possible points, which is consistent with the American Heart Association (AHA) certification standards and the Food and Drug Administration (FDA) criteria for a food to be designated as healthy or low in saturated fat. In the meats, poultry, seafood, dairy and nuts matrix of FIG. 6, the criterion (≦1.5 g) to receive the highest possible points is more stringent than the AHA certification standards for meats and seafood, and the FDA healthy criteria. Consumption of saturated fat is associated with an increased risk of heart disease.

3. Cholesterol—listed as Cholesterol on Nutrition Facts panel. In the general foods and beverages matrix of FIG. 5, products must contain ≦15 mg of cholesterol (5% DV) in order to not be penalized with negative points. This criterion is more stringent than the AHA certification standards and the FDA criteria for a food to be considered healthy or low in cholesterol. Likewise, in the meats, poultry, seafood, dairy and nuts matrix of FIG. 6, the criterion to receive the highest possible points (≦60 mg) is stricter than the AHA certification standards for these types of foods, and the FDA healthy definition.

4. Added sugars—refers to added, caloric (nutritive) sweeteners only. This term does not apply to naturally occurring, endogenous sugars or artificial sweeteners. Sugars must be identified as an ingredient using one or more of the keywords listed below. If a sugar or sweetener keyword is flagged then the gram value listed as Sugars on the Nutrition Facts panel is multiplied by 4 to arrive at the kilocalories contributed by free sugars. This number is then divided by the total number of kilocalories to obtain the percent of kilocalories contributed by sugars.

Added Sugars:
  Sugar
  Corn syrup
    High fructose corn syrup (HFCS)
    High dextrose corn syrup
  Dextrose or glucose
  Fructose or levulose
  Honey
  Lactose
  Maltodextrin
  Maltose or malt sugar
  Maple syrup or maple sugar
  Molasses
  Sucrose
    Raw sugar
    Granulated sugar
    Brown sugar
    Confectioner's sugar
    Dehydrated, evaporated or concentrated cane juice
    Dehydrated, evaporated or concentrated beet juice
    Invert sugar
    Turbinado sugar
  Sugar alcohols
    Erythritol
    Hydrogenated glucose syrup
    Isomalt
    Lactitol
    Malitol
    Maltitol
    Mannitol
    Sorbitol
    Sorbitol syrup
    Xylitol
    Xylose
  Tagatose
  Trehalose Foods are awarded the highest possible points if they contain no added sugar. The remaining criteria are based on the World Health Organization's recommendation to limit added sugars to $\leq 10\%$ of total kilocalories, and the Institute of Medicine's recommendation to limit added sugars to $\leq 25\%$ of total kilocalories. In the general food and beverages model (FIG. 5), any food item which contains over 50% of kilocalories from added sugar receives minus (−) 10 points to prevent it from receiving a star rating.

5. Dietary fiber—listed as Dietary Fiber on Nutrition Facts panel. In the general foods and beverages matrix of FIG. 5 products must contain $\geq 3.75$ g of fiber (15% DV) in order to receive the highest possible score of 3. This threshold exceeds the FDA standard for a food to be considered a good source of fiber. The fiber element is removed from the meats, seafood, poultry and dairy matrix of FIG. 6 as these foods do not naturally contain fiber.

6. Added Sodium—listed as Sodium on Nutrition Facts panel. This element does not penalize foods which naturally contain low levels of sodium (i.e. green, leafy vegetables, and dairy products). The sodium content of foods is only evaluated if additional sodium (as sodium chloride) has been added to the product by a food manufacturer or processor. Thus the keyword "salt" must be listed as an ingredient. If this keyword is flagged, then the gram value listed as sodium on the Nutrition Facts panel is evaluated. For all foods and beverages, the criterion ($\leq 120$ mg-5% DV) for a product to be awarded the highest possible points is slightly more conservative than the FDA standard for a food to be considered low in sodium, and far exceeds the AHA certification standards and the FDA healthy criteria. The remaining cutoffs for fewer points are based on multiples of the 5% DV benchmark. Any food item which contains over 600 mg of sodium per 100 kcal serving is given minus (−) 10 points to prevent it from receiving a star rating.

7. Nutrient Density—pertains to any vitamin (i.e. Vitamin A, Vitamin C) or mineral (i.e. Calcium, Iron) that is permitted to be listed on the Nutrition Facts panel. These are typically the last nutrients listed in the nutrient section (often just below the last wide black bar), and are always followed by a percentage. A manufacturer may opt to list any for which the food item is a significant source.

Vitamins:
  Vitamin A
  Vitamin C
  Vitamin D
  Vitamin E
  Vitamin K
  Biotin
  Thiamin or thiamine
  Riboflavin
  Niacin
  Vitamin $B_6$
  Folic acid or folate
  Vitamin $B_{12}$
  Pantothenate or pantothenic acid
Minerals:
  Calcium
  Chromium
  Copper
  Fluoride
  Iodine
  Iron
  Magnesium
  Manganese
  Molybdenum
  Phosphorus
  Potassium
  Selenium
  Zinc The criterion used to receive the highest possible points in this element is based on the AHA certification standards and FDA healthy criteria, but is more conservative in that the food must contain $\geq 10\%$ of the DV for two nutrients, rather than one. Moreover, the AHA and FDA standards include fiber as a nutrient, while the present invention includes fiber separately with its own weighting points.

8. Whole grain—products which contain $\geq 51\%$ whole grain ingredients by weight are currently considered to be whole grain by the FDA. To determine whether a product is whole grain, the product must have $\geq 1.5$ g fiber per 100 kcal serving and contain at least one of the following key words in the ingredients:

Whole grains:
- Amaranth
- Brown rice
- Buckwheat or kasha, buckwheat groats
- Cracked wheat or bulgur or bulghur
- Emmer
- Farro
- Grano
- Kamut
- Millet
- Milo
- Oatmeal
- Popcorn
- Quinoa
- Sorghum
- Spelt
- Teff
- Triticale
- Wheat berries
- Whole wheat (flour)
- Whole oat (flour)
- Whole (grain) corn or cornmeal (yellow and white)
- Whole rye
- Whole or rolled oats
- Wild Rice Whole grain foods are awarded bonus points in keeping with the AHA, the Dietary Guidelines for Americans, and Healthy People 2010 recommendations, which all recommend three servings of whole grains per day. Whole grain foods are associated with many long term health benefits including reduced risks of heart disease, diabetes, stroke, and many forms of cancer.

The following are detailed descriptions of nutritional elements that may optionally also be considered, with currently known limitations in doing so noted. However, the present invention contemplates the development of a matrix or matrixes incorporating weightings for such optional nutritional elements as any limitations noted are resolved.

1. Protein—may be included, but is not currently for several reasons. Protein is not a focus of any of the major health organizations nor is it included in any of their dietary recommendations. The 2005 US Dietary Guidelines for Americans likewise do not include specific recommendations for protein. In the US, people generally over consume this macronutrient. Thus, protein deficiency is extremely rare. Additionally, protein is found in negligible or trace amounts in many foods (i.e. produce, sweets). Thus it makes more sense to consider protein as a component of the total diet, rather than as a percentage of individual foods. Finally, there is presently no long term data on the safety and health effects of increased protein intake as recommended by many recent fad diets.

2. Total fat—as is the case for protein, total fat is not a component of the dietary recommendations of the major health organizations and is thus not currently included in the weighting matrix described herein. Focus has shifted away from total fat as many studies have now shown that it is the type of fat in the diet, rather than the total amount, that is linked with disease. In particular, trans fats and saturated fats are associated with increased risk for certain diseases while mono- and polyunsaturated fats are associated with reduced risk. The key is to substitute these latter "good" fats for the former "bad" fats.

3. Omega-3 fatty acids—these important nutrients are not included as an element in the scoring algorithm primarily due to feasibility issues. Omega-3 fatty acids are not currently listed on the Nutrition Facts panel for food products. Moreover, they cannot be found in the ingredient list if they naturally occur in a product (i.e., salmon, walnuts). While the AHA does recommend including at least two servings of fish per week (particularly fatty fish) to provide omega-3 fatty acids, they do not include omega-3 fatty acids per se in their food certification program, nor in their dietary recommendations. The scoring algorithm may be modified to include these nutrients, as they have documented anti-inflammatory and disease-fighting properties, as information becomes more widely available.

4. Monounsaturated fat—was omitted from the current algorithm as it is not consistently listed on all products. (It is optional for manufacturers to list this nutrient on the Nutrition Facts panel.) However, the process of the present invention may be modified to incorporate such information as it becomes available.

5. Phytochemicals (i.e., polyphenols, lycopene)—were omitted from the scoring algorithm for several reasons. There are many phytochemicals known to have positive health effects and it is not possible to create an objective and exhaustive list. Moreover, some manufacturers create brand specific versions of phytochemicals, and then give them a trademarked named which is used exclusively on their products. One example is NutraFlora$^R$ (similar to inulin) which is used in Silk soy milk brand products. Capturing all of these keywords may be difficult for purposes of completeness. Limited food data on particular phytochemicals may be found in the USDA special interest databases. However, these databases are very limited (<1000 foods each); thus, inclusion of this data would unfairly award bonus points only to foods for which such information is provided. As this data has not been incorporated into the main USDA nutrient database, it has not been included in the example scoring algorithm described herein. Further, there are no standard dietary recommendations or requirements for phytochemicals at this time. Thus any criteria used to assign points in the scoring algorithm would have to be arbitrarily set. However, the current algorithm could be modified to include such phytochemicals.

6. Phosphates (phosphoric acid)—are too pervasive in the food supply, and the evidence linking excessive phosphorus consumption from soft drinks with diminished bone health is equivocal at this time. Moreover, phosphoric acid is found predominately in dark colored soft drinks but not in light colored beverages. Thus inclusion of this element would make lighter-colored sodas appear healthier than darker ones. However, the current algorithm could be modified to include such additives.

7. Live, active cultures—are omitted from the model as a positive point because it is not possible at this time to ensure that products listing these in their ingredients were meeting the government-stipulated standard of identity. Per the FDA standard of identity, in order for a refrigerated product to be called "yogurt," it must be produced by culturing permitted dairy ingredients with a bacterial culture, which contains *Lactobacillus bulgaricus* and *Streptococcus thermophilus*. In addition to the use of bacterial cultures required by the FDA standard of identity, live and active culture yogurts may contain other safe and suitable food grade bacterial cultures. Yogurts containing live and active cultures must contain 100 million cultures per gram at the time of manufacture, and frozen yogurt products must contain 10 million cultures per gram at the time of manufacture. After reviewing numerous yogurt items it was discovered that there are many labeling differences among manufacturers. A number of manufacturers list cultures in the ingredients; some do not list any cultures but have opted to use the National Yogurt Association (NYA) Live & Active Cultures seal which ensures the FDA standard; and some use both. For example, the manufacturer of one sample lists the six cultures used in their manufacturing and they meet the standard (verified by calling their corporate office), but do not display the NYA seal. Conversely, the manufacturer of a second sample does not list the cultures in the ingredient panel, but does use the NYA seal. However, the current algorithm could be modified to include live, active cultures.

8. Phytosterols (stanols/sterols)—the model omits as a positive point phytosterols at this time, but could be modified to include them. The FDA standard of identity and the scientific literature suggest that the level of phytosterols needed to promote health could not be derived from the Nutrition Facts Panel or ingredient list at this time and that phytosterols, when added to food items such as margarine and yogurt ("functional foods"), serve the primary purpose to act as a cholesterol lowering agent.

9. Nitrates/nitrites—could be used to reduce the algorithm score when listed in the ingredients. At this time, however, the scientific literature suggests that the negative risk associated with additive dietary nitrite/nitrate consumption is inconclusive and that the necessary data cannot be derived from the Nutrition Facts Panel or ingredient list. Additionally a number of manufacturers have begun adding sodium erythorbate or sodium ascorbate, antioxidants that inhibit the nitrosation effect of nitrites on secondary amines, thereby possibly reducing the negative risk associated with these additives.

The scoring step 209 performed through the scoring function 50 preferably includes carrying out an algorithm to generate a single numerical value or score based on the weighting points assigned to the nutritional elements. The algorithm is a selectable equation to determine a single score, which score is then assigned a star designation. Specifically, using the scoring algorithm of the scoring step 209 and either or both of the matrixes of FIGS. 5 and 6, the score for a particular food item is the total of the points assigned by the matrix. A group assignment designation step 210 of the method 200 of FIG. 3 uses a chart, such as the chart of FIG. 7, to assign group designations on the zero-to-three stars format described herein based on the score calculated. Other group assignment designations may be employed without deviating from the scope of the invention.

Figure 7:
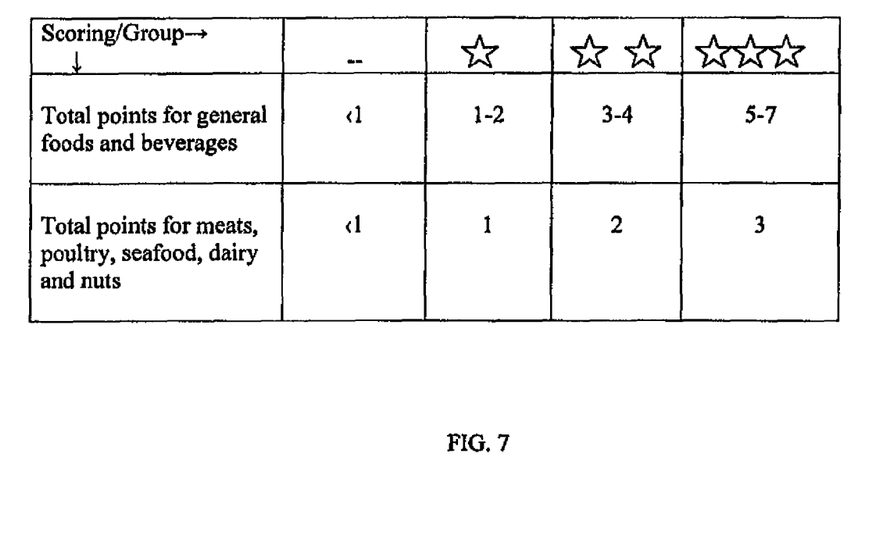
FIG. 7 is a chart for grouping assignments based on scores calculated, showing ranges of scores associated with grouping designations.

Three example food products, each having its own particular nutritional values, shown herein illustrate the scoring algorithm using the matrixes of FIGS. 5 and 6, and the chart of FIG. 7. The three examples are presented in table form herein, with Tables 1A and 1B developed for a cereal product, Tables 2A and 2B for a soup product, and Tables 3A and 3B for a popcorn product. For each of the example products, the nutritional information taken from the product's Nutritional Facts Panel is presented, along with the nutritional information standardized/normalized to a 100 kilocalorie serving size, in the A table. The standardized nutritional values for each product are then matched to the point scoring matrix of the applicable ones of FIGS. 5 and 6, the points established, and a final score are presented in the B table.

TABLE 1A

Nutrition Facts Panel

| Nutritional Element Name | Manufacturer Serving Size: 110.0 kilocalories (110.0 kcal) Quantity (as shown) | Standardized Serving Size 100.0 kilocalories (100 kcal) Quantity (as standardized) |
|---|---|---|
| Saturated fat | 0 g | 0 g |
| Trans fat | 0 g | 0 g |
| Cholesterol | 0 mg | 0 mg |
| Sodium | 280 mg (12% of total DV) | 254.6 mg (11% of total DV) |
| Dietary fiber | 3 g (11%) | 2.73 g (10%) |
| Sugars | 1 g | 0.9 g |
| Protein | 3 g | 2.7 g |
| Kilocalories (kcal) from fat | 15 | 13.6 |
| Total fat | 2 g (3%) | 1.8 g (3%) |
| Potassium | 95 mg (3%) | 86.4 mg (3%) |
| Total carbohydrate | 22 g (7%) | 20 g (6%) |
| Other carbohydrate | 18 g | 16.4 g |

| | Manufacturer Serving Size: 110.0 kilocalories (110.0 kcal) | Standardized Serving Size 100.0 kilocalories (100 kcal) |
|---|---|---|
| Vitamin A | 10% | 9% |
| Vitamin C | 10% | 9% |
| Calcium | 10% | 9% |
| Iron | 45% | 41% |
| Vitamin D | 10% | 9% |
| Copper | 2% | 2% |
| Magnesium | 10% | 9% |
| Niacin | 25% | 23% |
| Phosphorus | 10% | 9% |
| Vitamin B12 | 25% | 23% |
| Vitamin B6 | 25% | 23% |
| Zinc | 25% | 23% |
| Riboflavin | 25% | 23% |
| Thiamin | 30% | 27% |
| Folic Acid | 50% | 45% |

TABLE 1B

| Element No. | Nutritional Element | Standardized Quantity from Table A | Points |
|---|---|---|---|
| 1. | Trans fat | 0 g | 0 |
| 2. | Saturated fat | 0 g | 0 |
| 3. | Cholesterol | 0 g | 0 |
| 4. | Added sugar | 3.6% | −1 |
| 5. | Dietary fiber | 2.73 g | 2 |
| 6. | Added Sodium | 254.6 mg | −2 |
| 7. | Nutrient density | 8 nutrients (10% of DV) | 3 |
| 8. | Whole grain | Yes | 1 |
| | Total score | | 3 |

TABLE 2A

Nutrition Facts Panel

| Nutritional Element Name | Manufacturer Serving Size: 200.0 kilocalories (200.0 kcal) Quantity (as shown) | Standardized Serving Size 100.0 kilocalories (100 kcal) Quantity (as standardized) |
|---|---|---|
| Saturated fat | 2 g (10% of DV) | 1 g (5% of DV) |
| Trans fat | 0 g | 0 g |
| Cholesterol | 10 mg (3%) | 5 mg (2%) |
| Sodium | 1090 mg (45%) | 545 mg (22%) |

TABLE 2A-continued

Nutrition Facts Panel

| Nutritional Element Name | Manufacturer Serving Size: 200.0 kilocalories (200.0 kcal) Quantity (as shown) | Standardized Serving Size 100.0 kilocalories (100 kcal) Quantity (as standardized) |
|---|---|---|
| Dietary fiber | 3 g (12%) | 1.5 g (6%) |
| Sugars | 0 g | 0 g |
| Protein | 6 g | 3 g |
| Kilocalories (kcal) from fat | 70 | 35 |
| Total fat | 8 g (9%) | 4 g (6%) |
| Total carbohydrate | 26 g (9%) | 13 g (4%) |
| Calcium | 2% | 1% |
| Iron | 2% | 1% |

TABLE 2B

| Element No. | Nutritional Element | Standardized Ouantity from Table A | Points |
|---|---|---|---|
| 1. | Trans fat | 0 g | 0 |
| 2. | Saturated fat | 1 g | 0 |
| 3. | Cholesterol | 5 mg | 0 |
| 4. | Added sugar | 0% | 0 |
| 5. | Dietary fiber | 1.5 g | 1 |
| 6. | Added Sodium | 545 mg | −3 |
| 7. | Nutrient density | 0 nutrients (0% of DV) | 0 |
| 8. | Whole grain | No | 0 |
|  | Total score |  | −2 |

TABLE 3A

Nutrition Facts Panel

| Nutritional Element Name | Manufacturer Serving Size: 110.0 kilocalories (110.0 kcal) Quantity (as shown) | Standardized Serving Size 100.0 kilocalories (100 kcal) Quantity (as standardized) |
|---|---|---|
| Saturated fat | 0 g | 0 g |
| Trans fat | 0 g | 0 g |
| Cholesterol | 0 mg | 0 mg |
| Sodium | 250 mg (10% of total DV) | 227.3 mg (9% of total DV) |
| Dietary fiber | 4 g (16%) | 3.64 g (15%) |
| Sugars | 0 g | 0 g |
| Protein | 3 g | 2.7 g |
| Kilocalories (kcal) from fat | 15 | 13.6 |
| Total fat | 2 g (2%) | 1.8 g (2%) |
| Total carbohydrate | 20 g (7%) | 18.2 g (6%) |
| Iron | 4% | 4% |

TABLE 3B

| Element No. | Nutritional Element | Standardized Ouantity from Table A | Points |
|---|---|---|---|
| 1. | Trans fat | 0 g | 0 |
| 2. | Saturated fat | 0 g | 0 |
| 3. | Cholesterol | 0 mg | 0 |
| 4. | Added sugars | (N/A) | 0 |
| 5. | Dietary fiber | 3.64 g | 2 |
| 6. | Added Sodium | 227.3 mg | −1 |

TABLE 3B-continued

| Element No. | Nutritional Element | Standardized Ouantity from Table A | Points |
|---|---|---|---|
| 7. | Nutrient density | 0 nutrient (0% of DV) | 0 |
| 8. | Whole grain | Yes | 1 |
|  | Total score |  | 2 |

Based on the scoring shown, the first food product, the example cereal, has a score of 3, and from FIG. 7 as a "general food", is to be designated in the grouping presenting a two-star value. The second food product, the example soup, has a score of −2, and from FIG. 7, is to be designated in the grouping presenting a no-star value. Finally, the third food product, the example microwave popcorn product, has a score of 2, and from FIG. 7, is to be designated in the grouping presenting a one-star value.

As indicated, the steps of weighting of values (step 208) and scoring and grouping them (steps 209 and 210) may be performed by the scoring function 50 by including the recommendations of a panel of experts in nutrition. This panel includes nutritionists, researchers, doctors, professors, or others knowledgeable about nutrition. The panel reviews the gathered nutritional data as necessary for accuracy and provides advice about any changes and or updates based upon the expertise of its members. The panel also provides advice about the scoring and grouping system, including developing or improving the method or algorithm for determining the importance of particular nutritional elements. The panel may provide its input regularly, periodically, or on an ad hoc basis. This advice may be used to revise and update the scoring and grouping system and the grouping designations of products as necessary to keep them current.

It is to be understood that the number and type of the primary nutritional elements and the secondary nutritional elements may be different from the example sets shown in the matrix of FIG. 5, preferably dependent upon the recommendations of the advisory panel. Moreover, the number of weighting sets may be increased or decreased and the particular nutritional value ranges identified may be adjusted. Further, the scoring algorithm may be changed to adjust the importance of the primary or secondary nutritional elements. The representative matrix and scoring algorithm discussed herein is meant to be exemplar and not exhaustive.

Returning to FIG. 3, the step of assigning a group designation 210 includes selecting the appropriate designation from a predetermined list based upon the results of the scoring step 209. Designations may be as simple as the three-star system as described herein or may involve alternative designations. The groupings are then reported through the reporting function 60. The reporting step 212 involves the transmission of the groupings in usable form either in electronic form, orally, or in a written document. The reporting step 212 may be performed remotely or locally. The form of the report includes the designation assigned pursuant to the group assignment designation step 210 and may additionally include the output of the weightings of individual nutritional components and the details of the calculation of scorings using the algorithm of choice. The designations associated with the calculated scorings are then displayed 214 at the point of sale for the consumer to observe.

The steps described herein may be carried out through the identified functions of the system 10 as electronic functions performed through the computer system 100 based on computer programming steps. The functions configured to perform the steps described herein may be implemented in hardware and/or software. For example, particular software, firmware, or microcode functions executing on the computing devices can perform at least the data gathering function 20, data filtering function 30, data storing function 40, scoring function 50, and reporting function 60. Alternatively, or in addition, hardware modules, such as programmable arrays, can be used in the devices to provide some or all of those functions, provided they are programmed to perform the steps described.

The steps of the method of the present invention, individually or in combination, may be implemented as a computer program product or as computer-readable signals on a computer-readable medium, for example, a non-volatile recording medium, an integrated circuit memory element, or a combination thereof. Such computer program product may include computer-readable signals tangibly embodied on the computer-readable medium, where such signals define instructions, for example, as part of one or more programs that, as a result of being executed by a computer, instruct the computer to perform one or more processes or acts described herein, and/or various examples, variations and combinations thereof. Such instructions may be written in any of a plurality of programming languages, for example, Java, Visual Basic, C, or C++, Fortran, Pascal, Eiffel, Basic, COBOL, and the like, or any of a variety of combinations thereof. The computer-readable medium on which such instructions are stored may reside on one or more of the components of system 10 described above and may be distributed across one or more such components. Further, the steps of the method represented in FIG. 3, may be performed in alternative orders, in parallel and serially.

It is to be understood that various modifications may be made to the system 10 and related method without departing from the spirit and scope of the invention. Accordingly, other embodiments are within the scope of the claims appended hereto.

What is claimed is:

1. A computer-implemented method of assigning nutritional value ratings to a plurality of food products of the same and different type, the computer-implemented method using a computer system having (i) a plurality of computer-implemented functions, and (ii) one or more databases, the computer-implemented method comprising, for each food product, assigning a rating by:
    a) executing a data gathering function and a data filtering function of the computer system that
        (i) identifies nutritional data for a plurality of nutritional quality attributes of the food product, wherein caloric value is not a nutritional quality attribute of the food product; and
        (ii) stores the nutritional data in the one or more databases;
    b) establishing ranges of nutritional quality attribute values for each nutritional quality attribute;
    c) assigning a point value to each of the ranges of nutritional quality attribute values to establish the relative importance of each of the ranges, and storing the assigned point values in the one or more databases; and
    d) executing a scoring function of the computer system that is in communication with the one or more databases that
        (i) calculates a total nutritional quality score for the food product based on the point values of the nutritional quality attributes for the food product and a scoring algorithm, and
        (ii) assigns a nutritional value rating based on the total nutritional quality score, wherein each nutritional value rating corresponds to a nutritional quality score or a range of nutritional quality scores, and wherein the same scoring algorithm and rating correlations are used for different types of food products.

2. The method of claim 1 wherein the nutritional data is based on a normalized serving size.

3. The method of claim 2 wherein the serving size is normalized on a predetermined caloric value.

4. The method of claim 1 wherein the nutritional value rating is a designation of stars.

5. The method of claim 4 wherein the designation of stars ranges from zero to three.

6. The method of claim 1 wherein the nutritional quality attributes include trans fat, saturated fat, cholesterol, added sugars, added sodium, dietary fiber, vitamins, minerals and whole grain.

7. The method of claim 1 wherein the scoring algorithm adds up the assigned point values to obtain the nutritional quality score.

8. The method of claim 1 wherein a first plurality of types of food products uses a first correlation between each nutritional value rating and a nutritional quality score or a range of nutritional quality scores, and a second plurality of types of food products uses a second correlation between each nutritional value rating and a nutritional quality score or a range of nutritional quality scores, the same nutritional value ratings being used for the first and second plurality of types of food products.

9. The method of claim 1 further comprising the step of executing a reporting function of the computer system in communication with the scoring function that presents the nutritional value rating for each food product in a human readable printed form.

10. A computer-implemented system for assigning nutritional value ratings to a plurality of food products of the same and different type, the computer-implemented system comprising:
    (a) a data gathering function and a data filtering function of a computer system that
        (i) identifies nutritional data for a plurality of nutritional quality attributes of the food product, wherein caloric value is not a nutritional quality attribute of the food product;
        (ii) stores the nutritional data in one or more databases; and
        (iii) establishes ranges of nutritional quality attribute values for each nutritional quality attribute;
    (b) one or more of the databases of the computer system storing a point value assigned to each of the ranges of nutritional quality attributes to establish the relative importance of each of the ranges; and
    (c) a scoring function of the computer system in communication with the one or more databases that
        (i) calculates a total nutritional quality score for the food product based on the point values of the nutritional quality attributes for the food product and a scoring algorithm, and
        (ii) assigns a nutritional value rating based on the total nutritional quality score, wherein each nutritional value rating corresponds to a nutritional quality score or a range of nutritional quality scores, and wherein the same scoring algorithm and rating correlations are used for different types of food products.

11. The system of claim 10 wherein the nutritional data is based on a normalized serving size.

12. The system of claim 11 wherein the serving size is normalized based on a predetermined caloric value.

13. The system of claim 10 wherein the nutritional value rating is a designation of stars.

14. The system of claim 13 wherein the designation of stars ranges from zero to three.

15. The system of claim 10 wherein the nutritional quality attributes include trans fat, saturated fat, cholesterol, added sugars, added sodium, dietary fiber, vitamins, minerals and whole grain.

16. The system of claim 10 wherein the scoring algorithm adds up the assigned point values to obtain the nutritional quality score.

17. The system of claim 10 wherein a first plurality of types of food products uses a first correlation between each nutritional value rating and a nutritional quality score or a range of nutritional quality scores, and a second plurality of types of food products uses a second correlation between each nutritional value rating and a nutritional quality score or a range of nutritional quality scores, the same nutritional value ratings being used for the first and second plurality of types of food products.

18. The system of claim 10 further comprising a reporting function of the computer system in communication with the scoring function that presents the nutritional value rating for each food product in a human readable printed form.

19. A computer program product for assigning nutritional value ratings to a plurality of food products of the same and different type, wherein the computer program product includes computer-readable instructions tangibly embodied on a computer-readable medium that, when executed by a computer system, uses the computer system to perform a method comprising, for each food product, assigning a rating by:
   a. executing a data gathering function and a data filtering function of the computer system that
      i. identifies nutritional data for a plurality of nutritional quality attributes of the food product, wherein caloric value is not a nutritional quality attribute of the food product;
      ii. stores the nutritional data in one or more databases of the computer system; and
      iii. establishes ranges of nutritional quality attribute values for each nutritional quality attribute;
   b. assigning a point value to each of the ranges of nutritional quality attributes to establish relative importance of each of the ranges, and storing the point values for each of the ranges in the one or more databases; and
   c. executing a scoring function of the computer system that is in communication with the one or more databases that
      i. calculates a total nutritional quality score for the food product based on the point values of the nutritional quality attributes for the food product and a scoring algorithm, and
      ii. assigns a nutritional value rating based upon the total nutritional quality score, wherein each nutritional value rating corresponds to a nutritional quality score or a range of nutritional quality scores, and wherein the same scoring algorithm and rating correlations are used for different types of food products.

20. The computer program product of claim 19 wherein the nutritional data is based on a normalized serving size.

21. The computer program product of claim 20 wherein the serving size is normalized based on a predetermined caloric value.

22. The computer program product of claim 19 wherein the nutritional value rating is a designation of stars.

23. The computer program product of claim 22 wherein the designation of stars ranges from zero to three.

24. The computer program product of claim 19 wherein the nutritional quality attributes include trans fat, saturated fat, cholesterol, added sugars, added sodium, dietary fiber, vitamins, minerals, and whole grain.

25. The computer program product of claim 19 wherein the scoring algorithm adds up the assigned point values to obtain the nutritional quality score.

26. The computer program product of claim 19 wherein a first plurality of types of food products uses a first correlation between each nutritional value rating and a nutritional quality score or a range of nutritional quality scores, and a second plurality of types of food products uses a second correlation between each nutritional value rating and a nutritional quality score or a range of nutritional quality scores, the same nutritional value ratings being used for the first and second plurality of types of food products.

27. The computer program product of claim 19 wherein the computer readable instructions further perform a method comprising the step of executing a reporting function of the computer system in communication with the scoring function that presents the nutritional value rating for each food product in a human readable printed form.

28. A computer-implemented method of assigning nutritional value ratings to a plurality of food products of the same and different type, the computer-implemented method using a computer system having (i) a plurality of computer-implemented functions, and (ii) one or more databases, the computer-implemented method comprising, for each food product, assigning a rating by:
   a) executing a data gathering function and a data filtering function of the computer system that
      (i) identifies nutritional quantity data for a plurality of nutritional quality attributes of the food product, wherein caloric value is not a nutritional quality attribute of the food product;
      (ii) analyzes the data to determine its relative importance with respect to the nutritional value of the product;
      (iii) normalizes the nutritional quantity data for a predetermined caloric value to allow accurate comparison of different food products;
      (iv) stores the normalized nutritional data in the one or more databases including at least the Uniform Product Code and the normalized nutritional data; and
      (v) establishes ranges of nutritional quality attribute values for each nutritional quality attribute based on the normalized nutritional data;
   b) assigning a point value to each of the ranges of nutritional quality attributes to establish relative importance and storing the point values for each of the ranges in the one or more databases; and
   c) executing a scoring function of the computer system that is in communication with the one or more databases that
      (i) calculates a total nutritional quality score for the food product based on the point values of the nutritional quality attributes for the food product reflecting the food's value and a scoring algorithm assessing amounts of at least trans fat, saturated fat, cholesterol, added sugar, added sodium, dietary fiber, vitamins, minerals and whole grain, and
      (ii) assigns a nutritional value rating based on the total nutritional quality score, wherein each nutritional value rating corresponds to a nutritional quality score or a range of nutritional quality scores, and wherein the same scoring algorithm and rating correlations are used for different types of food products.

* * * * *